(12) United States Patent
Becker et al.

(10) Patent No.: US 9,254,109 B2
(45) Date of Patent: Feb. 9, 2016

(54) SELECTION OF A RADIATION SHAPING FILTER (71) Applicants: SIEMENS AKTIENGESELLSCHAFT, Munich (DE); KLINIKUM DER UNIVERSITATE MUNCHEN, Munich (DE)

(72) Inventors: Hans-Christoph Becker, Starnberg (DE); Thomas Flohr, Uehlfeld (DE); Bernhard Schmidt, Fuerth (DE)

(73) Assignee: SIEMENS AKTIENGESELLSCHAFT, Munich (DE)

( * ) Notice: Subject to any disclaimer, the term of this patent is extended or adjusted under 35 U.S.C. 154(b) by 144 days.

(21) Appl. No.: 14/023,626

(22) Filed: Sep. 11, 2013

(65) Prior Publication Data
US 2014/0112441 A1  Apr. 24, 2014

(30) Foreign Application Priority Data
Oct. 18, 2012  (DE) .......................... 10 2012 219 051

(51) Int. Cl.
*A61B 6/03* (2006.01)
*G21K 1/10* (2006.01)
(Continued)

(52) U.S. Cl.
CPC ............. *A61B 6/4035* (2013.01); *A61B 6/032* (2013.01); *A61B 6/035* (2013.01); *A61B 6/06* (2013.01);
(Continued)

(58) Field of Classification Search
CPC .......... A61B 6/032; A61B 6/035; A61B 6/06; A61B 6/40; A61B 6/4007; A61B 6/4014; A61B 6/4035; A61B 6/4042; A61B 6/405; A61B 6/4435; A61B 6/482; A61B 6/544; A61B 6/545; G21K 1/10
USPC .................................. 378/9, 16, 62, 156–159
See application file for complete search history.

(56) References Cited

U.S. PATENT DOCUMENTS 4,101,766 A    7/1978  Minami et al.
5,526,394 A *  6/1996  Siczek et al. .................... 378/37
(Continued)

FOREIGN PATENT DOCUMENTS

CN    101010039 A    8/2007
CN    101789277 A    7/2010
(Continued)

OTHER PUBLICATIONS

Hyun Joo Shin et al., "Radiation Dose Reduction via Sinogram Affirmed Iterative Reconstruction and Automatic Tube Voltage Modulation (CARE kV) in Abdominal CT," Korean J. Radiol. 14(6), Nov./Dec. 2013, 886-893.*
(Continued)

*Primary Examiner* — Allen C. Ho
(74) *Attorney, Agent, or Firm* — Harness, Dickey & Pierce, P.L.C.

(57) ABSTRACT

A method for selecting a radiation shaping filter is disclosed, which modifies the spatial distribution of the intensity and/or the spectrum of x-rays of an x-ray source of an imaging system. In an embodiment, anatomical measurement data of an object under examination is recorded, from which with the aid of the imaging system image data is created. The radiation shaping filter is selected automatically on the basis of the recorded anatomical measurement data of the object under examination. An imaging system, in which a radiation shaping filter is selected, is further disclosed.

19 Claims, 2 Drawing Sheets (51) Int. Cl.
*A61B 6/00* (2006.01)
*A61B 6/06* (2006.01)
*A61B 6/08* (2006.01)
*A61B 6/04* (2006.01)

(52) U.S. Cl.
CPC ... *A61B 6/08* (2013.01); *A61B 6/40* (2013.01); *A61B 6/4435* (2013.01); *A61B 6/482* (2013.01); *A61B 6/542* (2013.01); *A61B 6/544* (2013.01); *A61B 6/545* (2013.01); *G21K 1/10* (2013.01); *A61B 6/0457* (2013.01); *A61B 6/0492* (2013.01)

(56) References Cited

U.S. PATENT DOCUMENTS

| | | | | |
|---|---|---|---|---|
| 6,036,362 | A * | 3/2000 | Schmitt | 378/206 |
| 6,597,758 | B1 * | 7/2003 | Rosner | 378/53 |
| 6,614,878 | B2 * | 9/2003 | Bogatu et al. | 378/158 |
| 6,633,627 | B2 * | 10/2003 | Horiuchi | 378/156 |
| 6,968,030 | B2 * | 11/2005 | Hoffman | 378/5 |
| 6,990,171 | B2 * | 1/2006 | Toth et al. | 378/16 |
| 7,050,544 | B2 * | 5/2006 | Karlsson et al. | 378/158 |
| 7,076,029 | B2 * | 7/2006 | Toth et al. | 378/158 |
| 7,092,490 | B2 * | 8/2006 | Saladin et al. | 378/156 |
| 7,254,216 | B2 * | 8/2007 | Thandiackal et al. | 378/159 |
| 7,313,217 | B2 * | 12/2007 | Toth et al. | 378/20 |
| 7,330,535 | B2 * | 2/2008 | Arenson et al. | 378/158 |
| 7,430,282 | B2 * | 9/2008 | Mori et al. | 378/159 |
| 7,443,950 | B2 * | 10/2008 | Sendai | 378/37 |
| 7,535,987 | B2 * | 5/2009 | Matsuda | 378/7 |
| 7,613,276 | B2 * | 11/2009 | Sendai | 378/37 |
| 7,636,413 | B2 * | 12/2009 | Toth | 378/4 |
| 7,653,179 | B2 * | 1/2010 | Ramsauer et al. | 378/157 |
| 7,680,249 | B2 * | 3/2010 | Yuan | 378/158 |
| 7,715,522 | B2 * | 5/2010 | Goto et al. | 378/16 |
| 7,720,198 | B2 * | 5/2010 | Schliermann | A61B 6/08 378/108 |
| 8,005,284 | B2 * | 8/2011 | Sakaguchi | A61B 6/4441 382/131 |
| 8,218,728 | B2 * | 7/2012 | Karch | 378/98.11 |
| 8,284,903 | B2 * | 10/2012 | Yuan | 378/158 |
| 8,311,182 | B2 * | 11/2012 | Chandra et al. | 378/5 |
| 8,325,879 | B2 * | 12/2012 | Loos et al. | 378/156 |
| 8,571,178 | B2 * | 10/2013 | Sendai | 378/98.9 |
| 8,705,695 | B2 * | 4/2014 | Jabri et al. | 378/62 |
| 8,913,712 | B2 * | 12/2014 | Ninomiya | A61B 6/027 378/20 |
| 9,008,264 | B2 * | 4/2015 | Boone et al. | 378/51 |
| 2005/0031080 | A1 | 2/2005 | Klingenbeck-Regin et al. | |
| 2005/0154292 | A1 | 7/2005 | Tank | |
| 2008/0101538 | A1 | 5/2008 | Schliermann | |
| 2010/0189218 | A1 | 7/2010 | Sakaguchi et al. | |
| 2012/0128125 | A1 | 5/2012 | Jabri et al. | |
| 2012/0243655 | A1 | 9/2012 | Ninomiya et al. | |

FOREIGN PATENT DOCUMENTS

| | | |
|---|---|---|
| CN | 102688056 A | 9/2012 |
| DE | 10333295 A1 | 2/2005 |
| DE | 102004042790 A1 | 3/2006 |
| DE | 102011055465 A1 | 5/2012 |
| JP | H09-505498 A | 6/1997 |
| JP | 2009-25207 | 2/2009 |
| KR | 20050055599 A | 6/2005 |
| WO | WO 2012097801 A1 | 7/2012 |

OTHER PUBLICATIONS

Marilyn J. Siegel, "CT Dose Reduction Strategies Experience with Care (Auto) kV," IPR 2011.*
Korean Office Action dated Dec. 15, 2014 for corresponding KR Application No. 10-2013-123378.
Chinese Office Action and English translation thereof dated May 6, 2015.

* cited by examiner

FIG 2

SELECTION OF A RADIATION SHAPING FILTER

PRIORITY STATEMENT

The present application hereby claims priority under 35 U.S.C. §119 to German patent application number DE 102012219051.1 filed Oct. 18, 2012, the entire contents of which are hereby incorporated herein by reference.

FIELD

At least one embodiment of the invention generally relates to a method for selection of a radiation shaping filter, a method for controlling a radiation shaping filter device, a method for controlling the spectrum of an x-ray source, a method for controlling an x-ray imaging system and also an x-ray imaging system with a radiation shaping filter device.

BACKGROUND

A diaphragm is usually fitted between an x-ray source and the object under examination in x-ray imaging systems, especially in computed tomography systems, which initially defines the aperture of an x-ray bundle and the shape of a surface illuminated by the x-rays. A radiation shaping filter is frequently disposed after this diaphragm in the beam path of the x-rays, which can additionally change the x-rays in their intensity spatially or also spectrally. This generally involves planar filters which the entire x-ray beam (typically delimited by the diaphragm) passes through, without the filter in such cases having to have openings through which the x-rays could pass unchanged. Typically these filters are constructed of aluminum or Teflon.

For manipulation and further modification of the spectral or also spatial intensity distribution of the x-rays, different types of radiation shaping filters, such as so-called wedge filters or also bowtie filters (i.e. filters which additionally focus or widen out the x-rays with convex or concave-shaped surfaces, typically similar to the shape of a bowtie) are used, which can be inserted individually or in a combination of a number of radiation shaping filters into the beam path of the x-rays between an x-ray source and an object under examination. The intensity of x-rays can for example be reduced with the aid of a wedge filter transverse to the direction of propagation of the x-rays by a continuous attenuation value. The intensity minimum in such cases usually lies at the edge of an x-ray bundle used (delimited by the diaphragm). With the aid of a different filter type, such as the bowtie filter mentioned, at least local extremes of the x-ray intensity can be defined within the x-ray bundle for example.

There is also the possibility of defining the size or extent of the irradiated area or the areas of one or more radiation extremes. I.e. along with different types of radiation shaping filters there is also the possibility of selecting between different radiation shaping filters of the same type. For example, with filters of the same type, a choice can be made between "narrow filters" which spatially reduce the irradiated area, or "wide filters" and "very wide" filters, which might possibly expand the irradiated area or the area of an intensity extreme.

In addition it is likewise conceivable for the radiation shaping filter to especially influence the spectrum of the x-rays used (i.e. the spectral intensity distribution of the x-rays changes during its passage through the filter). For example in a spatial area determined by the filter the spectrum of the x-rays can be hardened, i.e. an intensity maximum of the x-rays is changed to smaller wavelengths. Likewise the spectrum of the x-rays might possibly be set softer with the aid of the filter in the predetermined spatial area (i.e. an intensity maximum is changed towards larger wavelengths).

The operator of an x-ray imaging system charged with taking an x-ray thus has the choice between a plurality of filters and their combination, in order to optimize the process of taking the x-ray. On the one hand the optimization can consist of guaranteeing the image quality of an image provided and on the other hand also of keeping the radiation load imposed on an object under examination when obtaining the image as low as possible. A corresponding optimization is largely based in such cases on the experience of the operator.

In the optimum case, for each use of the imaging system in respect of these optimization targets a suitable scan or examination protocol (i.e. a sequence of control steps) is stored, on the basis of which the imaging in the imaging system is controlled and which may possibly predetermine a radiation shaping filter to be used. If a scan protocol is not available for the application concerned, this must first be created based on the specialized knowledge of the operator. An optimum choice of radiation shaping filter in such cases may possibly not be guaranteed. Furthermore the assignment of radiation shaping filters to specific protocols is complex and hampers a simplification of the operation of an x-ray imaging system.

SUMMARY

At least one embodiment of the present invention is directed to improving or even optimizing the x-ray images in respect of their quality or of the load imposed on an object under examination by the x-ray imaging, especially to reduce unnecessary radiation load or image quality defects caused by the incorrect choice of radiation shaping filters.

A method for selecting a radiation shaping filter, a method for controlling a radiation shaping filter device, a method for controlling the spectrum of an x-ray source, a method for controlling an x-ray imaging system and an x-ray imaging system are disclosed.

In accordance with at least one embodiment of the invention, an improved method for choosing a radiation shaping filter or for determining a radiation shaping filter arrangement is proposed. The radiation shaping filter, which can especially be embodied as described in the introduction, in this case changes the spatial distribution of the intensity and/or the spectrum of x-rays of an x-ray source of an imaging system. The spectral change preferably likewise occurs spatially in respect of the wavelengths emitted by the x-ray source. A radiation shaping filter arrangement is to be understood as the spatial arrangement of one or more radiation shaping filters, which for example can also be described by the omission of one or more radiation shaping filters in a specific spatial area between x-ray source and object under examination.

In accordance with at least one embodiment of the invention, anatomical measurement data of an object under examination is recorded from which, in a further step, an image is to be recorded with the aid of the imaging system. In the description given below anatomical measurement data is to be understood as measurement data based on anatomical parameters such as shape, location or also structure of body parts, organs, tissue or cells. I.e. especially that the anatomical measurement data represents the said anatomical parameters directly or indirectly.

In particular, at least one embodiment of the inventive method can be used in an x-ray imaging system having a recording unit for recording anatomical measurement data and/or anatomical parameters (or parameter values). The recording unit in this case can be embodied as an interface, via which for example an anatomical parameter can be recorded directly if this is available for example as a directly measured parameter value or also as a directly identifiable parameter. In addition it is likewise conceivable for the recording unit to have the function of a parameter determination unit, which is embodied for generating or determining anatomical parameters or also parameter values from the anatomical measurement data, which are indirectly represented by the anatomical measurement data.

In accordance with a development of at least one embodiment of the invention, a method is proposed for controlling the spectrum of an x-ray source, wherein the control is undertaken on the basis of a radiation shaping filter selected using the inventive method or on the basis of a determined radiation shaping filter arrangement. Thus it is possible for example to determine an optimum working point of the x-ray imaging system as regards the radiation dose also the image quality and to control the spectrum of the radiation source accordingly.

BRIEF DESCRIPTION OF THE DRAWINGS

The invention will be explained below once again in greater detail with reference to the enclosed figures based on example embodiments. In this case the same components are provided in different figures with identical reference numbers. In the figures.

DETAILED DESCRIPTION OF THE EXAMPLE EMBODIMENTS

The present invention will be further described in detail in conjunction with the accompanying drawings and embodiments. It should be understood that the particular embodiments described herein are only used to illustrate the present invention but not to limit the present invention.

Accordingly, while example embodiments of the invention are capable of various modifications and alternative forms, embodiments thereof are shown by way of example in the drawings and will herein be described in detail. It should be understood, however, that there is no intent to limit example embodiments of the present invention to the particular forms disclosed. On the contrary, example embodiments are to cover all modifications, equivalents, and alternatives falling within the scope of the invention. Like numbers refer to like elements throughout the description of the figures.

Specific structural and functional details disclosed herein are merely representative for purposes of describing example embodiments of the present invention. This invention may, however, be embodied in many alternate forms and should not be construed as limited to only the embodiments set forth herein.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items.

It will be understood that when an element is referred to as being "connected," or "coupled," to another element, it can be directly connected or coupled to the other element or intervening elements may be present. In contrast, when an element is referred to as being "directly connected," or "directly coupled," to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Spatially relative terms, such as "beneath", "below", "lower", "above", "upper", and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, term such as "below" can encompass both an orientation of above and below. The device may be otherwise oriented (rotated 90 degrees or at other orientations) and the spatially relative descriptors used herein are interpreted accordingly.

Although the terms first, second, etc. may be used herein to describe various elements, components, regions, layers and/or sections, it should be understood that these elements, components, regions, layers and/or sections should not be limited by these terms. These terms are used only to distinguish one element, component, region, layer, or section from another region, layer, or section. Thus, a first element, component, region, layer, or section discussed below could be termed a second element, component, region, layer, or section without departing from the teachings of the present invention.

In accordance with at least one embodiment of the invention, an improved method for choosing a radiation shaping filter or for determining a radiation shaping filter arrangement is proposed. The radiation shaping filter, which can especially be embodied as described in the introduction, in this case changes the spatial distribution of the intensity and/or the spectrum of x-rays of an x-ray source of an imaging system. The spectral change preferably likewise occurs spatially in respect of the wavelengths emitted by the x-ray source. A radiation shaping filter arrangement is to be understood as the spatial arrangement of one or more radiation shaping filters, which for example can also be described by the omission of one or more radiation shaping filters in a specific spatial area between x-ray source and object under examination.

In accordance with at least one embodiment of the invention, anatomical measurement data of an object under examination is recorded from which, in a further step, an image is to be recorded with the aid of the imaging system. In the description given below anatomical measurement data is to be understood as measurement data based on anatomical parameters such as shape, location or also structure of body parts, organs, tissue or cells. I.e. especially that the anatomical measurement data represents the said anatomical parameters directly or indirectly.

In such cases the anatomical measurement data can be direct measured values of the anatomical parameters or the parameters themselves. For example the size of the patient could be measured directly as a parameter value or a specific body part also identified as a property parameter. Below, for the sake of simplicity, both anatomical parameters and also anatomical parameter values are to be covered by the expression "anatomical parameters", where no explicit distinction is made.

On the other hand, the anatomical measurement data can represent the anatomical parameters indirectly. For example the size of the patient could also be determined from images, topograms or other imaging of the patient, wherein the image or the topogram data in this case is to be seen as anatomical measurement data. I.e. the anatomical parameters can also be created or derived from the anatomical measurement data.

Finally, in accordance with at least one embodiment of the invention, the radiation shaping filter is selected or the radiation filter arrangement is determined on the basis of the recorded anatomical measurement data of the object under examination. The operator thus immediately obtains an appropriate suggestion for a radiation shaping filter arrangement.

In particular, it can be determined with the aid of at least one embodiment of the inventive method based on the anatomical measurement data which of the radiation shaping filters available for a planned x-ray imaging would be the most advantageous to select. As an alternative a proposal for an optimum radiation shaping filter arrangement can also be determined, so that only subsequently can the radiation shaping filters best adapted to the radiation shaping filter arrangement be selected from the available shaping filters. One result of the determination can also be that the imaging of the object under examination can be performed in the optimum manner without any kind of radiation shaping filters and thus the choice consists of whether or not to use any radiation shaping filter for the planned x-ray imaging. In addition it is also conceivable for the operator to receive a number of suggestions determined. These are easier to assess for the operator, since the number of radiation shaping filter arrangements determined is less than the total number of possible combinations available for disposing the existing radiation shaping filters.

The automatic determination or choice of a radiation shaping filter arrangement enables a manual determination of a filter arrangement to be dispensed with. Only after the automatic determination can a final confirmation step for selecting the filter arrangement be provided.

In particular, at least one embodiment of the inventive selection can be independent of the measurement protocol for activating the imaging system mentioned at the start. Preferably the imaging can also be controlled based on a unified scan or examination protocol in respect of the filter choice, so that the choice of an unsuitable radiation shaping filter can be largely excluded. Just one step can then be included for example in this unified measurement protocol, in which at least one embodiment of the inventive determination or choice of a radiation shaping filter or of a radiation shaping filter arrangement is made automatically. I.e. the imaging system is activated on the basis of the measurement protocol which comprises the step of automatic selection of a radiation shaping filter or the determination of a radiation shaping filter arrangement using at least one embodiment of the inventive method.

In at least one embodiment of the inventive method, the selected radiation shaping filter arrangement can then be automatically inserted in a further step into the beam path of the x-ray source of the imaging system. It is preferred, as mentioned at the outset, for the radiation shaping filter arrangement to be downstream from a diaphragm of the x-ray imaging system in the beam path of the x-rays. In such cases the radiation shaping filter arrangement—as mentioned—is introduced between the x-ray source and the object under examination to be imaged or possibly radiation shaping filters might be removed from the beam path. This can be done for example with the aid of suitable robotics, so that control instructions of the operator are also obsolete in this respect. The corresponding control steps can in their turn be elements of a suitable measurement protocol, which is then varied dynamically on the basis of the choices determined, in order for example to carry out the necessary control steps. As an alternative the introduction into the beam path of the x-rays of the radiation shaping filter arrangement determined can also be an element of the automatic selection method, so that it is sufficient for the measurement protocol, as mentioned above, to contain the step of automatic selection of the radiation shaping filter.

In particular, at least one embodiment of the inventive method can be used in an x-ray imaging system having a recording unit for recording anatomical measurement data and/or anatomical parameters (or parameter values). The recording unit in this case can be embodied as an interface, via which for example an anatomical parameter can be recorded directly if this is available for example as a directly measured parameter value or also as a directly identifiable parameter. In addition it is likewise conceivable for the recording unit to have the function of a parameter determination unit, which is embodied for generating or determining anatomical parameters or also parameter values from the anatomical measurement data, which are indirectly represented by the anatomical measurement data.

At least one embodiment of the inventive x-ray imaging system also has a selection unit for selecting a radiation shaping filter. In this case the selection unit is embodied to select or determine a radiation shaping filter or a radiation shaping filter arrangement automatically on the basis of anatomical measurement data (or of anatomical parameters determined therefrom). In particular the selection unit can be combined with a filter determination unit. The filter determination unit initially automatically determines one or more suggestions for selecting a radiation shaping filter arrangement on the basis of the anatomical measurement data. The radiation shaping filter is then chosen by the selection unit on the basis of the suggestions determined by the filter determination unit. As mentioned the selection unit can for example be embodied to detect a confirmation of the user of the x-ray system to make a final selection of a radiation shaping filter arrangement for a planned x-ray measurement. For example it is conceivable for the filter determination unit to be included in a selection unit or be constructed separately from the selection unit.

Further, especially advantageous embodiments and developments of the invention emerge from the dependent claims as well as the subsequent description, wherein the independent claims of one claim category can also be developed in a similar manner to the dependent claims of another claim category.

As mentioned, a selected radiation shaping filter arrangement, i.e. especially also an individual radiation shaping filter, can be introduced for example in the inventive method into the beam path of the x-ray source or can be removed from said beam path. This can be done for example by a radiation shaping filter device having an activation device or being connected to an activation device. The radiation shaping filter device is then embodied to automatically introduce a selected radiation shaping filter into the beam path of the x-ray source or to remove it from the beam path during operation. For this purpose the radiation shaping filter device has the robotics already discussed, i.e. in particular an automatic drive, which can for example be based on spring force, electrical energy, pneumatic or also hydraulic energy. The robotics or the radiation shaping filter device can receive the filter control signals which control the movement of the radiation shaping filter into or out of the beam path of the x-ray source, from the said activation unit.

The filter control signals are generated by the activation unit on the basis of the determined or selected shaping filter arrangement. For example the activation unit can be included in the selection unit. Thus in particular an option of automatic modification of a radiation shaping filter arrangement can be provided on a modular basis and based on anatomical measurement data.

The module can for example also include a radiation shaping filter, which can be modified by adding or omitting individual, preferably singular, especially preferably one-piece-construction filter elements. For example essentially planar, flat, preferably one-piece-construction filter elements can be combined into a radiation shaping filter, especially into a radiation shaping filter stack. The radiation shaping filter stack can for example be a variable wedge or bowtie filter. This especially offers the advantage of enabling an optimum radiation shaping filter arrangement to largely be realized with the aid of the modifiable radiation shaping filter, without having to deviate too far from the determined optimum radiation filter arrangement, as can for example be the case if only a specific number of radiation shaping filters is available.

The number of radiation shaping filters, which in accordance with the prior art can typically be simultaneously introduced into the beam path of the x-ray source, is typically two or three. Embodiments of the invention go beyond this. In a development which employs the modular construction principle there is therefore provision that for example more than three, preferably more than five and especially preferably more than ten radiation shaping filters can be introduced simultaneously into the beam path of the x-ray source. I.e. especially that the radiation shaping filter device is embodied to introduce the more than three, more than five or more than ten radiation shaping filters into the beam path of the x-rays, so that the x-rays of the x-ray source pass through said filters at the same time. The radiation shaping filters then preferably have correspondingly compact dimensions in order for example, in accordance with the modular construction principle, to form in combination a modifiable shaping filter, which can be modifiable both in the longitudinal direction of the patient but also in the transverse direction of the patient and which for example has the function of a wedge or bowtie filter. For example a majority of these radiation shaping filters used in the module are embodied as thin filter layers, which are thinner than conventional filters since they can in fact be combined with further filters.

In a development, at least one anatomical parameter of the object under examination can be determined automatically directly or also indirectly (i.e. as mentioned measured directly or also derived or generated from anatomical measurement data). Preferably all anatomical parameters included for automatic selection are determined automatically. Thus for example a fully automatic selection or determination of a radiation shaping filter or of a radiation shaping filter arrangement can be undertaken, which for example merely comprises the confirmation steps mentioned.

For example the selection or determination of the radiation shaping filter arrangement is done automatically on the basis of a measurement, especially on the basis of the size and/or the thickness of the object under examination.

Furthermore the kind or the type of the area under examination, such as for example a heart or an arm, can be a basis for the inventive selection or determination of the radiation shaping filter or of the radiation shaping filter arrangement. In particular the spatial position or also structural parameters, such as the type of tissue for example, can contribute to this foundation.

Preferably in such cases the area under examination or also the dimensions of the object under examination can be determined automatically, so that manual entries relating to this data can be omitted.

Furthermore the selection or determination of the radiation shaping filter or of the radiation shaping filter arrangement can for example be undertaken automatically on the basis of the expected attenuation of the x-rays by the object under examination to be imaged. For example the weight of the patient could be measured and their geometrical dimensions determined in order to determine an expected attenuation.

In particular the expected attenuation of the x-rays can be determined automatically here. In this case it is possible, by automatic weighing of the patient and measuring the size of the patient, to derive the expected attenuation of the x-rays and also vice versa.

The direct measurement of the expected attenuation of the x-rays, by means of a topogram data for example, also provides the opportunity for deriving the anatomical parameters mentioned, such as weight or size of the patient for example, or other structural information.

The described anatomical measurement data such as weight, size and examination area can in such cases be taken into account in different ways in the determination of the radiation shaping filter arrangement.

The selection of radiation shaping filters can be determined for example for a heart or cranial image essentially by the examination area. The examination area in this case essentially determines the attenuation of the x-rays to be expected and also the spectrum of the x-rays to be used. For cranial imaging rather softer x-rays can be provided for example, i.e. the radiation shaping filter then varies the x-ray spectrum compared to the spectrum created by the radiation source towards a softer spectrum. The spatial distribution can be selected for example so that the object under examination or an (examination) area of the object under examination receives a high dose and the rest of the patient a lower dose in relation to the high dose. The option also exists of adapting the shape of the intensity profile (i.e. the spatial distribution of the x-rays) to the form of the object under examination and/or the area under examination.

Based on the area under examination, a basic choice of a radiation shaping filter arrangement can then be made, which for example essentially predetermines the (spatial) shape (i.e. the spatial intensity distribution) and the spectrum of the x-rays transmitted by the radiation shaping filter. The parameters "weight" and "size" of the object under examination (or other dimensions of the object under examination) then only contribute subsequently, for example to determine the precise shape of the irradiated area. Subsequently means in this case that, as a result of these parameters, a variation of the shape of the irradiated area does not exceed the percentage change (related to the surface dimension of the irradiated area) which is obtained by the basic selection compared to an irradiation of the patient without radiation shaping filters. In relation to the spectrum, a displacement of an intensity maximum of the x-rays can then take place "downstream" which does not exceed the percentage variation (in relation to the wavelength), which is obtained by the basic choice compared to an irradiation of the patient without radiation shaping filter.

For other x-ray imaging however, the size and the weight of the object under examination can definitively determine the choice of the radiation shaping filter. In particular size and weight can definitively determine the utilization of a measurement field of the CT system and thus the basic choice of the radiation shaping filter. The anatomical measurement data relating to the examination area in this case is only taken into account downstream (i.e. as described above, the deviations of the surface dimension and/or of the spectrum do not exceed the achieved variations which are obtained by the basic choice based on the size and/or the weight in percentage terms), for selecting a suitable spectrum of the x-rays or of the irradiated area for example.

Preferably the anatomical measurement data includes a preferably anatomically-created image of the object under examination.

For example the image of the object under examination can be recorded with the aid of a camera, which image data is created on the basis of light in the visible wavelength spectrum or also in the IR wavelength spectrum. Preferably the image of the patient can then be triggered automatically, for example at a specific position of a patient couch, especially when the patient is located in the planned position for an x-ray image.

Furthermore it is also conceivable for the image to be a topogram data, i.e. a rapidly determined overview image of the expected attenuation of the x-rays by the object under examination.

Furthermore ultrasound images, MRT images or also other preliminary information are also considered for example, in order especially to determine preferably automatically the location of an organ or other anatomical parameters, e.g. in combination with the camera image mentioned.

In particular anatomical measurement data can automatically be recorded in this way, with the aid of which the overall radiation load of the patient in respect of the planned x-ray examination can be minimized. This can be done for example by dispensing with the creation of topogram data for controlling the x-ray imaging system.

For example further components of the x-ray imaging system can be controlled based on this anatomical measurement data or based on the selection of a radiation shaping filter.

In accordance with a development of at least one embodiment of the invention, a method is proposed for controlling the spectrum of an x-ray source, wherein the control is undertaken on the basis of a radiation shaping filter selected using the inventive method or on the basis of a determined radiation shaping filter arrangement. Thus it is possible for example to determine an optimum working point of the x-ray imaging system as regards the radiation dose also the image quality and to control the spectrum of the radiation source accordingly.

This can for example be done with an x-ray imaging system with an x-ray control unit, which controls the spectrum of the x-ray source assigned to the x-ray shaping filter on the basis of the selected x-ray shaping filter. This in turn improves the possibilities of excluding incorrect operation of the x-ray imaging system.

It is especially included in at least one embodiment of the invention that the described selection or control methods can be applied for one or more x-ray sources of the imaging system, to which in each case a radiation shaping filter arrangement or a radiation shaping filter is assigned. In such cases it is conceivable for a separate x-ray control unit, a separate selection unit, a separate filter determination unit, a separate recording unit, a separate x-ray control unit and also a separate radiation shaping filter device to be used for a respective x-ray source of the imaging system and thus for these components to be present more than once. Thus a flexible independent selection and determination of the radiation shaping filter or of the radiation shaping filter arrangement is possible for the different radiation sources. In addition a separate retrofitting of the corresponding components can be possible for example.

Over and above this it is also conceivable for one or more of these units or devices to be assigned jointly to a number of x-ray sources of the imaging system. Thus for example interactions of the determined radiation shaping filter arrangement of an x-ray source with the determined radiation shaping filter arrangement of another x-ray source can be taken into account especially easily.

In such cases it is also possible to integrate one or more of these components, units or devices into one another in order to achieve an optimized construction of the x-ray imaging system and to simplify taking account of the interactions mentioned.

Figure 1:
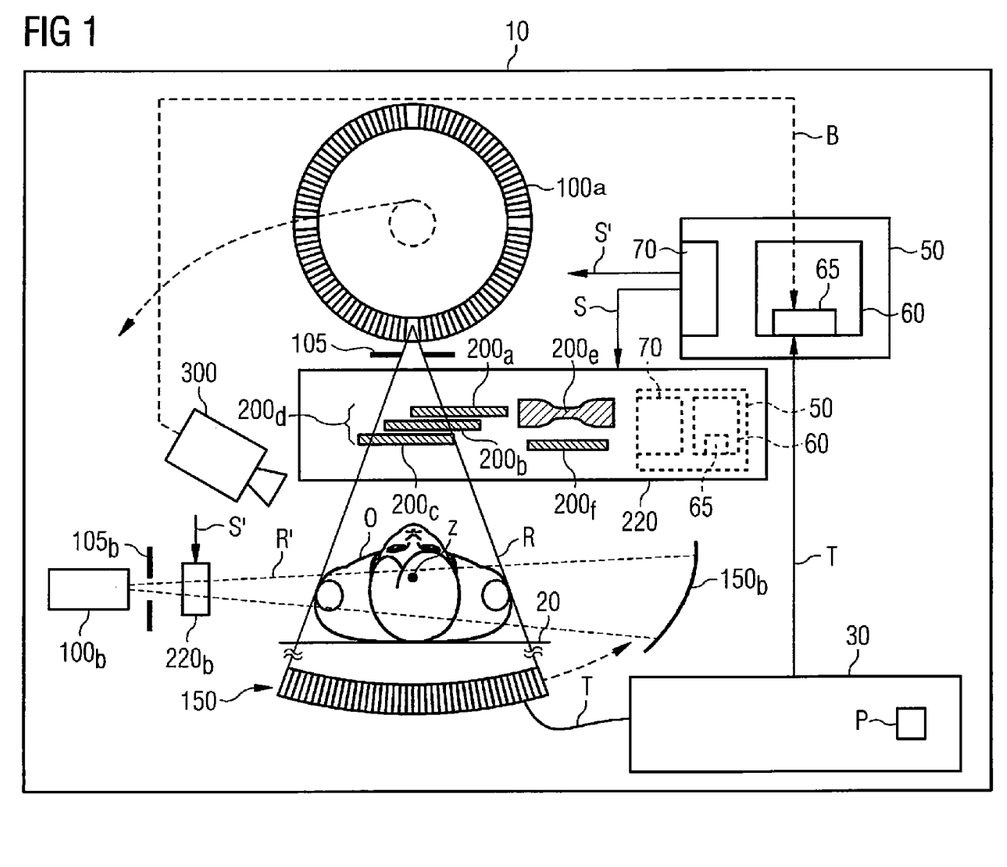
FIG. 1 shows a first example embodiment of an imaging system with an x-ray source and an x-ray detector, wherein an arrangement of radiation shaping filters which is introduced into the beam path of the x-ray source is chosen automatically.

FIG. 1 shows a schematic cross sectional diagram perpendicular to a system axis z of an x-ray imaging system, here a CT system 10, for creation of two-, three- or multidimensional computed tomography image data. The CT system 10 essentially consists in this case of a usual scanner, in which on a gantry an x-ray detector 150 circulates around a measurement chamber with an x-ray source 100a lying opposite the x-ray detector 150. This is indicated schematically by dashed lines with an arrow at their end. A patient support device or a patient table 20 is located in front of the scanner, the upper part of which, with an object under examination O or patient O located thereon, can be moved relative to the scanner in the direction of the system axis z, in order to move the patient O relative to the x-ray detector 150 through the measurement chamber. The system axis z in this case simultaneously forms a common circulation axis of the x-ray detector 150 and the x-ray source 100. The scanner and the patient table 20 are controlled by a control device 30, from which control data is sent out via a normal interface, in order to control the CT system 10 in accordance with predetermined measurement protocols P.

It should be emphasized at this point that the methods described here can basically also be used with other CT systems, e.g. with a detector forming a complete ring. Furthermore the methods can also be used with another x-ray imaging system.

The raw data (i.e. x-ray projection data) acquired by the x-ray detector 150 is transferred to the measurement data interface of the control device 30. This raw data is then further processed in an image reconstruction device of the control device 30 realized on a processor in the form of software, which reconstructs raw data from image data for example.

The completed computed tomography image data or volume image data created on the basis of the raw data is then transferred to an image data interface, which then for example stores the created image data in a memory of the control device 30 or outputs it in the usual way on a screen of the control device 30 or the data is fed via an interface into a network connected to the CT system 10, for example an archive system (PACS) or radiological information system (RIS) or corresponding images are stored in mass storage present there or output to printers connected there. The data can also be further processed in any other way and then stored or output.

The recorded raw data can especially also involve so-called topogram data T, which is included for creating a fast overview recording of the patient O and for planning a computed tomography recording.

This topogram data T, as is explained in greater detail below within the context of the invention, can be included as anatomical measurement data for selecting a radiation shaping filter or for selecting a radiation shaping filter arrangement.

As explained above, different anatomical parameters can be taken directly and also indirectly from the topogram data T. This is done with the aid of a detection unit 65, which accepts the topogram data T and determines anatomical parameters from the data. For example, the topogram data T directly contains the attenuation of x-rays to be expected as a result of the properties of the patient O. The attenuation to be expected locally at a specific detector position in this case is especially dependent on anatomical parameters such as for example the dimensions of the patient O, i.e. especially on its size, its weight, the position and structure of organs, body parts or tissue, so that these anatomical parameters can be determined or generated directly from the topogram data T. For example anatomical parameter values for the location, size or also structure of the head of the patient O can be obtained or created from the topogram data T.

In particular the position of an area under examination can also be determined on the basis of the topogram data T, as is described below more precisely in conjunction with FIG. 2, in order for example to explicitly make possible the recording of an image of the head, the heart also the lungs.

As an alternative or in addition to the topogram data T, anatomical measurement data from which again anatomical parameters or parameter values can be determined, can also be established in the form of image data B, which for example is created by a camera 300. The camera 300 shown generates anatomical measurement data in the form of images or image data B of the patient O on the basis of light in the visible wavelength range, while the patient O is located on the patient table 20. This imaging can likewise be sufficient to create parameters for the location, size or also structure of the head of the patient O.

In order for example to be able to determine the location of organs or other tissue, the image data B can be combined with preliminary information, which for example can be provided by ultrasound images or earlier MRT/CT images. In such cases it is also conceivable for the ultrasound images to be only recorded during or after the recording of the image data B and subsequently for example to be combined with the image data B or also topogram data T. The radiation load caused by the planned x-ray examination is not increased in such cases, since this preliminary information is available in any event and for example can be made available via the said PACS system as anatomical measurement data.

Furthermore the weight of the patient O could likewise be determined for example in advance or for example with the aid of a balance (i.e. based on a mass comparison) or weighing device (i.e. based on the weight force) of the patient table 20 or also be estimated from the image data B.

The anatomical measurement data including image data B and/or topogram data T made available in this way, i.e. especially the image data B or also the topogram data T, is then accepted by the detection unit 65, evaluated if necessary and transferred in the form of anatomical parameters to a filter determination unit 60.

A first alternative to anatomical determination of a radiation shaping filter arrangement with the aid of the filter determination unit 60 is provided as described below.

On the basis of the anatomical measurement data (or the anatomical parameters and/or parameter values associated therewith) the optimum geometry of the x-rays R emitted by the x-ray source 100a can be determined or selected. Likewise this data defines the optimum wavelength spectrum of the x-rays R. The filter determination unit 60 determines, on the basis of the anatomical measurement data in relation to size, weight and examination area, an optimum shape in respect of the spatial distribution of the x-rays and the spectrum of the x-rays used. For example for a CT recording of a heart a radiation shaping filter can be used which—as explained at the start—is "narrower" than with abdomen or thorax images, in order for example to direct the full x-ray intensity onto the area under examination such as the heart for example and reduce the dose in the periphery. In this case the examination area for example definitively specifies the geometrical shape and also the spectral distribution of the optimum x-rays R for the planned imaging.

In addition the size and the bulk (or the weight) of the patient can definitively influence both the spectral distribution of the x-rays R and also the geometrical shape of the distribution of optimum x-rays R. For example for obese patients O once again a "wider" radiation shaping filter can be used as opposed to the standard filter provided for normal-weight patients used for thorax recordings for example. At the same time a hardened spectrum of x-rays R would be used so that the optimum spectrum of the x-rays R is also influenced by the size or the weight of the patient O.

Conversely, for example for children, the parameters "size" or "bulk" can specify the use of "narrower radiation shaping filters" with a "softer" spectrum of the x-rays than for adults.

In the first alternative, based on the optimum shape determined, i.e. an optimum spatial distribution in respect of intensity and spectral components of the x-rays R, in a subsequent step with the aid of the filter determination unit 60 based on the available radiation shaping filters 200a, 200b, 200c, 200d, 200e, 200f, an optimum radiation shaping filter arrangement can be determined.

In a second alternative the filter determination unit 60 can also operate so that initially, in an initial step of filter determination, possible radiation shaping filter arrangements are determined on the basis of the available radiation shaping filters 200a, 200b, 200c, 200d, 200e, 200f. Preferably for example based on a standard filter or a standard filter arrangement for a specific examination area, a list with all combination options of the available radiation shaping filters 200a, 200b, 200c, 200d, 200e, 200f can be created. In their turn the possible changes of x-rays R for each of the possible radiation shaping filter arrangements can be calculated from the possible radiation shaping filter arrangements. Based on the possible changes, the filter determination unit 60 then determines the change which, based on the anatomical measurement data, is best suited for carrying out the respective planned x-ray imaging. By contrast with the first alternative, the determination of an optimum shape of x-rays R is thus restricted only to the available options for modifying the x-rays R, and e.g. based on a standard filter arrangement.

In the example embodiment a selection unit 50, as well as the detection unit 65 mentioned, includes the filter determination unit 60 and an activation unit 70, which on the basis of the radiation shaping filter arrangement determined with the aid of the filter determination unit 60, transfers filter control signals S to a radiation shaping filter device 220. The selection unit 50 selects the determined radiation shaping filter 200d for a subsequent planned CT measurement. For this purpose the user receives one or more suitable suggestions, which can be confirmed or if necessary also modified by the user.

The radiation shaping filter device 220 has robotics, which on the basis of the filter control signals S, brings the selected filters 200a, 200b, 200c, 200d to a location in the beam path of the x-rays determined with the aid of the filter determination unit 60.

As is indicated by the dashed line, the selection unit 50 can also be a component of the radiation shaping filter device 220. The selection unit 50 can also be realized in another way, for example at least partly in the form of software on a processor of the CT system 10 and especially on a processor of the control device 30.

In the example embodiment shown in FIG. 1 a (wedge-shaped) filter, i.e. a wedge filter 200d, is moved into the beam path of the x-rays R after a diaphragm 105 between the x-ray source 100a and the patient O. The remaining radiation shaping filters 200e, 200f present remain unused for the planned CT measurement.

With the aid of the diaphragm 105 a bundle of x-rays R is initially defined, which irradiates the patient O. For example a cone or wedge beam is usually delimited with the aid of the diaphragm 105. The wedge filter 200d disposed after the diaphragm 105 determines the spatial intensity of the x-rays R such that maximum radiation intensity of the x-rays R strikes the area of the heart of the patient O. The intensity distribution is set here along an axis which runs perpendicular to the system axis z.

As is indicated in the merely schematic diagram, the wedge filter 200d comprises a number of flat, square radiation shaping filters 200a, 200b, 200c. These are stacked and aligned in relation to their flat sides so that an almost wedge-shaped radiation shaping filter results. Going beyond the precision of the merely schematic diagram, the number of the square radiation shaping filters 200a, 200b, 200c can for example be ten or more filters. The radiation shaping filter arrangements with a number of flat radiation shaping filters 200a, 200b, 200c thus forms an adjustable radiation shaping filter or wedge filter 200d, which can be adapted especially easily to the optimum shape of the x-rays R, i.e. in this case as mentioned directs the greatest intensity of the x-rays R onto the heart of the patient O.

In the example embodiment the radiation shaping filters 200a, 200b, 200c are each manufactured in one piece from different materials. The radiation shaping filter 200a in this example is formed from aluminum, while the radiation shaping filter 200b consists of titanium and the radiation shaping filter 200c for its part, unlike the other filters 200a, 200b is made of copper. As a result of the different transmission properties of the different materials for x-rays R, for each material a different attenuation of specific wavelengths of the spectrum of x-rays R is produced. Thus it is possible, with the aid of the wedge filter 200d not only to modulate the intensity of the x-rays R spatially, but also the spectrum of the x-rays R. For example in this way an optimum wavelength distribution for computed tomography imaging of a heart can be achieved by selecting a radiation shaping filter 200d.

A further x-ray source 100b is merely shown schematically, with the aid of which for example the CT system 10 can be operated in a dual-source mode. The x-rays R' of the x-ray source 100b are likewise restricted by a diaphragm 105b and pass through radiation shaping filters which are assigned to a radiation shaping filter device 220b. After the patient O has been irradiated the x-rays R' are then detected with the aid of a separate x-ray detector 150b assigned to the x-ray source 100b. The radiation shaping filter device 220b is likewise activated with the aid of filter control signals S' in the manner described in relation to the radiation shaping filter device 220 by the activation unit 70. In such cases the activation unit 70 and also all further components assigned to the selection unit 50 are used both for activating the radiation shaping filter device 220 and also for activating the radiation shaping filter device 220b. For example a common optimum shape for the x-rays R, R' can be determined, which in relation to the planned x-ray examination is optimum as regards the image quality and/or the radiation load on the patient.

Figure 2:
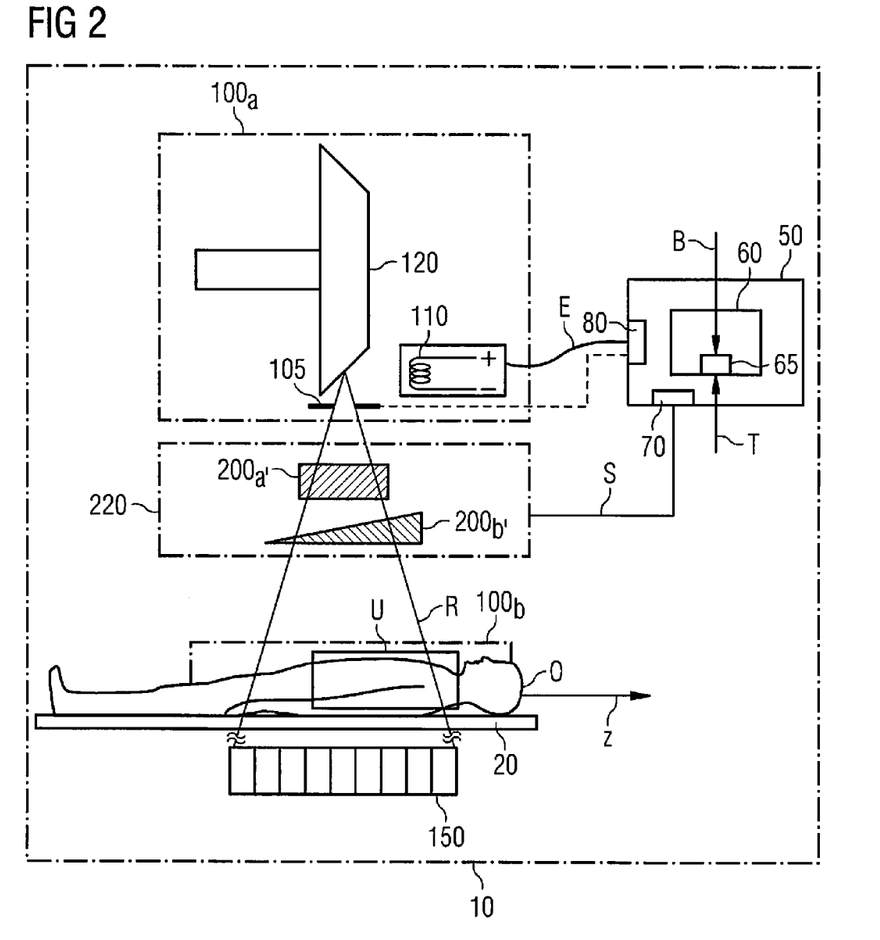
FIG. 2 shows a second example embodiment of an imaging system with a number of x-ray sources wherein, in addition to the first example embodiment, an x-ray source is controlled on the basis of the selected radiation shaping filter arrangement.

FIG. 2 shows a development of the CT system 10 shown in FIG. 1, likewise in a schematic view, but this time however as a schematic longitudinal section along the system axis z. As well as the further components described in relation to FIG. 1, the CT system 10 likewise has two x-ray sources 100a, 100b, which can each be activated independently of one another so that for example it is possible to operate the CT system 10 in what is referred to as dual-source mode.

In accordance with the method described in relation to FIG. 1, in this example embodiment a wedge filter 200b' and a bowtie filter 200a' are selected with the aid of the selection unit 50 based on anatomical measurement data. The anatomical measurement data especially contains information about the location of the examination area U, which is defined in this case by a planned three-dimensional computed tomography image of the stomach area. The location of this examination area U can be determined especially on the basis of the image data B or also the topogram data T. For automatic determination of the location of the examination area U characteristic signatures can be included for example from the topogram data T or also from the image data B, which for example identify an arm or the head or also the stomach area.

The appropriate acceleration voltage or also the tube current of the x-ray sources 100a, 100b for the planned computed tomography imaging, in this case of the stomach area, can for example be determined with known methods such as CARE kV or also CARE DOSE 4D from SIEMENS, so that for example a basic setting of these parameters can be determined for the planned computed tomography imaging. In the example embodiment the x-ray source 100a, 100b is also controlled appropriately for the radiation shaping filter arrangement determined. For reasons of clarity this is only indicated schematically for the x-ray source 100a.

As mentioned in relation to FIG. 1, an optimum shape and spatial intensity distribution of the x-rays R for a planned computed tomography measurement can be determined with the aid of the filter determination unit 60. If the opportunities for modification of the x-rays R with the aid of the existing radiation shaping filters 200a', 200b' deviate greatly from the optimum form determined, an adaptation to the optimum form can be improved with the aid of controlling the x-ray source 100a itself.

For this purpose an electron source 110 receives spectrum control signals E, which can modify the acceleration voltage for a target 120 or also the tube current of the electron source 110. For this purpose the selection unit 50 has an x-ray control unit 80, which determines suitable spectrum control signals E on the basis of the selected radiation shaping filter arrangement.

In the same way it is likewise conceivable for the aperture of the x-rays R to be controlled with the aid of the diaphragm 105 on the basis of the selected filter arrangement. As is merely shown by dashed lines, the x-ray control unit 80 could also suitably control the aperture of the diaphragm 105 for this purpose.

In conclusion it is pointed out that the features of all the example embodiments or developments disclosed in figures can be used in any given combination. It is likewise also pointed out in conclusion that the x-ray imaging system described in detail here, the method for selecting a radiation shaping filter, the method for controlling a radiation shaping filter device and the method for controlling the spectrum of an x-ray source merely involve example embodiments which can be modified by the person skilled in the art in a wide variety of ways without departing from the area of the invention. Furthermore the use of the indefinite article "a" or "an" does not exclude the features concerned being able to be present a number of times.

Likewise the term "unit" does not exclude the components concerned consisting of a number of interoperating subcomponents, which can possibly also be spatially distributed.

What is claimed is:

1. A method for selecting a radiation shaping filter arrangement, configured to modify a spatial distribution of at least one of intensity and spectrum of x-rays of an x-ray source of an imaging system, the method comprising:
    recording anatomical measurement data of an object under examination; and
    selecting the radiation shaping filter arrangement, automatically, based upon the anatomical measurement data of the object under examination, the radiation shaping filter arrangement including more than three individual radiation shaping filters arranged in a radiation shaping filter stack.

2. The method of claim 1, wherein the selecting includes, determining at least one anatomical parameter or parameter value of the object under examination, and
    selecting the radiation shaping filter arrangement based on the at least one anatomical parameter or parameter value of the object under examination.

3. The method of claim 2, wherein the selecting includes, determining a plurality of anatomical parameters and a plurality of parameter values, and
    selecting the radiation shaping filter arrangement based on the plurality of anatomical parameters and the plurality of parameter values.

4. The method of claim 2, wherein the selecting select the radiation shaping filter arrangement is based upon at least one of a measurement of the object under examination and a measurement of a spatial location of an examination area.

5. The method of claim 1, wherein the selecting selects the radiation shaping filter arrangement based upon at least one of a measurement of the object under examination and a measurement of a spatial location of an examination area.

6. The method of claim 1, wherein the selecting selects the radiation shaping filter arrangement based on an expected attenuation of the x-rays by the object under examination.

7. The method of claim 6, wherein selecting includes,
    determining the expected attenuation of the x-rays automatically.

8. The method of claim 1, wherein the recording includes,
    recording an image of the object under examination.

9. The method of claim 8, wherein the recording records an image of the object under examination with a camera, which creates the image on the basis of light in at least one of a visible wavelength range and an IR range.

10. The method of claim 8, wherein the recording includes,
    generating a topogram.

11. The method of claim 1, further comprising:
    bringing, automatically, the selected radiation shaping filter arrangement into a beam path of the x-ray source.

12. The method of claim 1, further comprising:
    controlling the spectrum of the x-ray source on the basis of the selected radiation shaping filter arrangement.

13. The method of claim 1, wherein the method is used for a number of x-ray sources of the imaging system.

14. The method of claim 1, further comprising:
    controlling the imaging system based on the selected radiation shaping filter arrangement and a measurement protocol.

15. An x-ray imaging system, comprising:
    an x-ray source;
    a control device configured to record anatomical measurement data; and
    a selection unit configured to automatically select a radiation shaping filter arrangement on the basis of the anatomical measurement data, the radiation shaping filter arrangement including more than three individual radiation shaping filters arranged in a radiation shaping filter stack.

16. The x-ray imaging system of claim 15, wherein the radiation shaping filter arrangement further includes,
    an activation unit configured to automatically bring the selected radiation shaping filter arrangement into a beam path of the x-ray source during operation.

17. The x-ray imaging system of claim 16, wherein the control device is configured to, on the basis of the selected radiation shaping filter arrangement, control a spectrum of the x-ray source assigned to the radiation shaping filter arrangement.

18. The x-ray imaging system of claim 15, wherein the control device is configured to, on the basis of the selected radiation shaping filter arrangement, control a spectrum of the x-ray source assigned to the radiation shaping filter arrangement.

19. The x-ray imaging system of claim 15, wherein the control device is configured to record at least one of anatomical parameters and parameter values.

* * * * *